US005817458A

United States Patent [19]
King et al.

[11] Patent Number: 5,817,458
[45] Date of Patent: Oct. 6, 1998

[54] REAGENT SYSTEM FOR DETECTING HIV-INFECTED PERIPHERAL BLOOD LYMPHOCYTES IN WHOLE BLOOD

[75] Inventors: Chester F. King, Frederick; Robert A. Hallowitz, Gaithersburg, both of Md.

[73] Assignee: The Avriel Group, AMCAS Division Inc.; a part interest

[21] Appl. No.: 732,782

[22] Filed: Oct. 15, 1996

[51] Int. Cl.⁶ .............................. C12Q 1/70; A01N 1/02; G01N 33/53; G01N 33/567

[52] U.S. Cl. .................................. 435/5; 435/2; 435/721; 436/512; 436/513; 436/518; 436/526; 436/531

[58] Field of Search .................................. 435/2, 5, 7.21, 435/7.32, 239, 803; 436/512, 513, 518, 531, 526

[56] References Cited

U.S. PATENT DOCUMENTS

| | | | |
|---|---|---|---|
| 4,487,830 | 12/1984 | Coates | 435/7 |
| 4,659,678 | 4/1987 | Forrest et al. | 436/512 |
| 4,731,337 | 3/1988 | Luotola et. al. | 436/526 |
| 4,777,145 | 10/1988 | Luoto | 436/526 |
| 4,935,147 | 6/1990 | Ullman, V | 210/695 |
| 5,166,050 | 11/1992 | Shriver | 435/5 |
| 5,217,895 | 6/1993 | Ohno | 435/240.27 |
| 5,238,810 | 8/1993 | Fujiwara | 435/5 |
| 5,245,015 | 9/1993 | Fung | 530/388.35 |
| 5,279,936 | 1/1994 | Vorpahl | 435/6 |
| 5,411,863 | 5/1995 | Miltenyl | 435/6 |
| 5,541,072 | 7/1996 | Wang et al. | 435/7.21 |
| 5,543,289 | 8/1996 | Miltenyi | 435/2 |

OTHER PUBLICATIONS

Burke et al., "Measured of the Fals Positive Rate in a Screening Program for Human Immunodeficiency Virus Infections", *New England J. Med.,* 319:961–964 (1988).

Busch et al., "Consistent Sequential Detection of RNA, Antigen and Antibody in Early HIV Infection: Assessment of the Window Period", *XI International AIDS Conference* (1996).

Chanh et al., "Human immundeficiency virus gp 120 glycoprotein detected by a monoclonal antibody to synthetic peptide", *Eur. J. Immunol.,* 16:1465 (1986).

Centers for Disease Control, "Update" Serologic Testing for Antibody to Human Immunodeficiency Virus, *MMWR,* 36:833–840 (1988).

Cohen et al., "Transmission of Retroviruses by Transfusion of Screened Blood in Patient Undergoing Cardiac Surgery", *New England J. Med.,* 320:1172–1176, (1989).

Dalgeleish et al., *Science,* 312:763–767 (1984).

Dutton et al., "Iron–dextran antibody conjugates: General method for simultaneous staining of two components in high–resolution immunelectron microscopy", *Natl. Acad. Sci,* 76:3392–3396 (1979).

Gallo, "The First Human Retrovirus", *Scientific American,* 255:88–98 (1986).

Gallo, "The AIDS Virus", *Scientific American,* 256:47–56 (1987).

Gostling et al., "Monoclonal Antibodies to gp110 and gp41 of Human Immunodeficiency Virus", *J. Clin. Microbiol.,* 25:845 (1987).

Ithakissios et al., "Use of Protein Containing Magnetic Microparticles in Radioassays", *Clin. Chem.,* 23:2072–2079 (1977).

Birkmeyer, et al.: Application of Novel Chromium Dioxide Particle . . . : Clin. Chem.: v. 33/9: pp. 1543–1547, 1987.

Luk et al.: Rapid and sensitive detection of salmonella . . . : J. Immun. Meth.: 137: pp. 1–8, 1991.

Levy, et al.: Isolation of lymphatic retrovirus . . . : Science: vol. 225: pp. 840–842, 1984.

Gallo, et al.: Frequent detection and isolation of cytopathic . . . : Science: vol. 224: pp. 500–503, 1984.

Levy, et al.: Isolation of lymphocytopathic retroviruses . . . : Science: vol. 225: pp. 840–842, 1984.

Gallo, et al.: Frequent detection and isolation of cytopathic . . . :Science: vol. 224: pp. 500–503, 1984.

Birkmeyer, et al.: Application of NOvel Chromium Dioxide Particles . . . : Clin. Chem.: v. 33/9: pp. 1543–1547, 1987.

Luk, et al.: Rapid and sensitive detection of salmonella . . . : J. Immun. Meth.: 137: pp. 1–8, 1991.

Dalgleish et al., "The CD4 (T4) antigen is an essential component of the receptor for the AIDS retrovirus", *Nature,* vol. 312 (20/27), pp. 763767, Dec. 1984.

*Primary Examiner*—Lynette F. Smith
*Assistant Examiner*—Brett Nelson
*Attorney, Agent, or Firm*—Millen, White, Zelano & Branigan, P.C.

[57] ABSTRACT

Fluorometric immunological assay method for detection of HIV-1 infection in which Murine anti-gp120 monoclonal antibodies coupled to paramagnetic microspheres (14) and Fluorescein conjugated anti-gp120 polyclonal antibodies IgG (16) are incubated in a few drops of whole blood diluted in 0.5 cc phosphate buffered saline (10). After incubation for 5 minutes, the HIV-infected peripheral blood lymphocytes (18) will be coated with both the Murine anti-gp120 monoclonal antibodies coupled to paramagnetic microspheres (14) and Fluorescein conjugated anti-gp120 polyclonal antibodies IgG (16) at exposed gp120 antigens (20) binding sites. At the time of measurement said HIV- infected peripheral blood lymphocytes (18) will be pulled against the wall of the measurement vessel by means of a magnetic gradient (26). The cells adhering to the vessel wall are illuminated at 488 nm monochromatic light by a focused light source (28) and the resultant emitted fluorescence is imaged, measured and recorded.

17 Claims, 2 Drawing Sheets

REAGENT SYSTEM FOR DETECTING HIV-INFECTED PERIPHERAL BLOOD LYMPHOCYTES IN WHOLE BLOOD

CROSS REFERENCES TO RELATED APPLICATIONS

The invention is to be used with another invention known as a cartridge antigen test, which allows for the collection and mixing of blood with reagents in one package, and which can be viewed on a fluorescent microscope.

The invention is to be used with another invention known as the Mehica GP120 Dectector, an automated fluorescent microscope system that incubates and reads cartridge antigen tests.

1. Background—Field of Invention

The present invention relates to the early diagnosis of Human Immunodeficiency Virus (HIV) infections. More particularly, the invention provides compositions and methods for utilizing commercially available, high affinity and highly specific magnetically coupled monoclonal antibodies to the envelope surface glycoprotein of HIV-1 known as gp120, along with commercially available FITC conjugated polyclonal antibodies to gp120 for the purpose of isolating and fluorescing HIV-1 infected peripheral blood lymphocytes in whole blood.

2. Background—Description of Prior Art

The present invention relates generally to methods and materials useful in the early diagnosis of infection with HIV. More particularly, the invention provides compositions and methods for utilizing commercially available, high affinity and highly specific magnetically coupled monoclonal antibodies to the envelope surface glycoprotein of the HIV-1 known as gp120, along with commercially available FITC conjugated polyclonal antibodies to gp120 for the purpose of isolating and fluorescing HIV-1 infected peripheral blood lymphocytes in whole blood.

The state of the art with respect to the epidemiology and immunology of the causative agent of Auto-immune Deficiency Syndrome (AIDS) in humans is well summarized in: Laurence, "The Immune System and AIDS," Scientific American, 254, 12, 84–93 (1985); Gallo, "The First Human Retrovirus," Scientific American, 256, 12, 88–98, (1986); Gallo, "The AIDS Virus," Scientific American, 256, 1, 47–56 (1987); Levy, et.al., Science, 225, 840–842 (1984); "Mobilizing against AIDS," Institute of Medicine, National Academy of Sciences, Harvard University Press (Cambridge, Mass., 1986); and Lane, et. al., Ann. Rev. Immunol., 3, 477–500 (1985).

The role of the CD4 surface glycoprotein of human T lymphocytes in infection by HIV has been extensively studied as represented by: Dalgeleish, et al., Science, 312, 763–767 (1984); Klatzmann, et al., Science, 225, 767–768 (1984); Klatzmann, et al., Science, 225, 59–62 (1984); McDoual, et al., J. Immunol., 135, 3151–3162 (1985); and Maddon, et al., Cell, 47, 333–348 (1986).

Infection of a T cell with HIV-1 follows from interaction between an epitope borne by HIV-1 and the CD4 receptor which is located on the T cell surface. The epitope on HIV-1 is borne by the envelope glycoprotein gp120 (molecular weight 120 kilodaltons). The glycoprotein gp120 is structurally exposed on the outside of the HIV-1 envelope. The gp120 binds to the CD4 antigens which exist on the cell surface of the helper T cells, etc., and in addition to providing the fusion point between the virus and the T helper cell, gp120 possesses activity which results in syncytium formation, the mechanism of cell to cell infection with HIV-1, as described in detail in U.S. Pat. No. 4,725,699.

In light of the above background information regarding HIV and AIDS, it can be deduced that antibodies specific for the envelope of the virus, which plays such an important role in the establishment of the viral infection, could have great significance in identifying the most crucial cell-bound antigens on the surface of infected cells in the peripheral blood.

A number of research groups have reported successful development of murine monoclonal antibody specific for gp120. For example, T. C. Can, et al. (Eur. J. Immunol. 16:1465, 1986) reported that they chemically synthesized a portion of the peptide chain of gp120 and then prepared monoclonal antibodies (mAbs) specific for the synthetic peptide. They employed those mAbs in an indirect fluorescent antibody technique and reported they were able to detect HIV infection with greater sensitivity than was possible with the reverse transcriptase determination technique. Additional reports of murine anti-gp120 mAbs have been reported by Gostling et al., J. Clin. Mocrobiol., 25, 845 (1987) and Matsushida et al., Medical Immunol., 14, 307, (1987).

The present invention is concerned with a fluoremetric immunoassay in which a pair of manufactured non-competitive antibodies to gp120 are utilized. One antibody (mAb) is coupled to paragmagnetic particles, while the second is in conjugate with FITC. The present invention takes advantage of the technology of immunomagnetic separation developed over the past 15 years to enrich or separate out of a mixture of cells, specific cellular components based on their specific immunological markers. The prior art is exemplified by U.S. Pat. Nos. 4,77,145; 4,731, 337; 5,186,827; 5,238,810; 5,279,936; 5,411,863; and 4,935, 147.

In these inventions particular methods are disclosed for separating a substance from a liquid medium using magnetic particles. None of these inventions, however, are specific for the process of using immunomagnetic particles for the diagnosis of HIV in whole blood. The present invention relies upon the commercial availability of high affinity anti-gp120 mAbs coupled with magnetic particles and a second non-competitive anti-gp120 polyclonal antibody (pAb) conjugated with FITC to fluorimetrically "tag" an HIV-infected cell and then magnetically separate it from uninfected cells in whole blood.

Of particular importance to the background of the present invention is the consideration of factors that demonstrate the importance of creating a diagnostic system which takes advantage of the above described molecular biology of HIV infection. It is also important to understand the need for the present invention based upon the limitations posed by current screening and confirmatory test protocols which are still mainly dependent upon host immune response to HIV infection by antibody production.

Testing serum for antibodies to HIV is currently the most cost-effective and accurate method of screening for and confirmation of infection. References concerning this include: Centers for Disease Control, "Update: Serologic Testing for Antibody to Human Immunodeficiency Virus." MMWR, 36, 833–40 (1988); Schwartz, J. S., Dans, P. E., Kinosian, B. P., "Human Immunodeficiency Virus Test Evaluation, Performance and Use." JAMA, 259, 2574–9 (1988); Burke, D. S., Brundage, J. F., Redfield, R. R., et al. "Measurement of the False Positive Rate in a Screening Program for Human Immunodeficiency Virus Investions." New England Journal of Medicine, 319, 961–4 (1988);

Cohen, N. D., Munoz, A., Reitz, B. A., et al., "Transmission of Retroviruses by Transfusion of Screened Blood in Patients Undergoing Cardiac Surgery." New England Journal of Medicine, 320, 1172–6 (1989); and MacDonald, K. L., Jackson, J. B., Bowman, R. J., et al., "Performance Characteristics of Serologic Tests for Human Immunodeficiency Virus Type 1 (HIV-1) Antibody Among Minnesota Blood Donors. Public Health and Clinical Implications." Ann. Intern. Med., 110, 617–21 (1989).

HIV antibody tests have their limitations. Usually antibodies to HIV appear within 3–6 months and as early as 6–8 weeks after infection, but silent infections have been documented in which seroconversion has occurred as late as 3 years from the moment of exposure. Therefore, because an infected person does not develop antibodies immediately, a negative test result cannot rule out HIV infection.

It has been shown that the majority (90%) of people first testing positive for HIV will develop AIDS within one year. This strongly suggests that the average person identifying HIV infection has been positive for an average of 8–9 years, in view of the fact that the average interval between infection and AIDS is 9–10 years.

This is particularly problematic because of the behavioral studies indicating that a person practicing high risk behaviors is likely to seek testing within days or a few weeks of the high risk behavior. That person is then likely to forget about HIV and continue risky behavior based on the false reassurance of a negative test performed before seroconversion was even possible.

The consequences of the above observations are:

1. The majority of people practicing intermittent high risk behaviors tend to seek reassurances very shortly after committing such behaviors.
2. They get reassurance and false security because of false-negative tests based on as yet undetectable antibody levels.
3. The majority of infected people continue intermittent or continuous high risk behaviors for 8–9 years after becoming infected.
4. These people are, therefore, transmitting HIV for 8–9 years.
5. If affordable, accurate testing could be accomplished within the brief interval between risky behavior and seroconversion, a significant increase in early HIV detection would be likely.
6. Therefore, affordable early detection would create a significant reduction in the high prevalence of HIV transmission by the falsely assured and oblivious people in the 90% majority cited above.

In a study of consistent sequential detection of RNA, antigen and antibody in early HIV infection, sequential appearance in blood of HIV RNA, HIVag, and HIV antibody was found. Data derived from testing seroconversion panels demonstrate a consistent sequential rise in the concentrations of HIV RNA followed by HIV antigen (p24), followed by anti-HIV in early HIV infection. Based on the timing of the appearance of RNA and antigen it was concluded that HIV RNA and HIVag could be used to confirm early infection. RNA and/or HIVag tests were concluded to be potentially useful for earlier detection of HIV infection (e.g. blood screening). The results of this study were published by Busch, M., Schumacher, Richard T., Stramer, S., et al., "Consistent Sequential Detection of RNA, Antigen and Antibody in Early HIV Infection: Assessment of the Window Period" Irwin Memorial Blood Center, San Francisco, Calif., Boston Biomedical, Inc., Bridgewater, Mass. Poster presented at XI International AIDS Conference, Vancouver, BC, July, 1996.

Efforts have been made to close this "window" between exposure and antibody detectability. The p24 antigen test has already been mandated for use by all registered blood and plasma centers because of a partial closure of the "window" achieved by this method. However, in the best-case scenario, p24 antigen detection realistically only closes the window by 6–7 days. Since a significant rate of viral reproduction occurs within the first week of infection causing the presence of the envelope glycoprotein gp120 bearing lymphocytes in the peripheral blood, detection of blood-bound gp120 is an effective means to close the "window" even further than the p24 test.

FURTHER DESCRIPTION OF THE RELATED ART

A method for determining the concentration of substances in biological fluids (e.g., drugs, hormones, vitamins and enzymes) wherein magnetically responsive, permeable, solid, water insoluble, microparticles are employed is disclosed in U.S. Pat. No. 4,115,534. Functional magnetic particles formed by dissolving a mucopolysaccharide such as chitosan in acidified aqueous solution containing a mixture of ferrous chloride and ferric chloride is disclosed in U.S. Pat. No. 4,285,819. The microspheres may be employed to remove dissolved ions from waste aqueous streams by formation of chelates. U.S. Pat. No. 3,933,997 describes a solid phase radio immunoassay for digoxin where anti-digoxin antibodies are coupled to magnetically responsive particles.

Small magnetic particles coated with an antibody layer are used in U.S. Pat. No. 3,970,518 to provide a large and widely distributed surface area for sorting out and separating select organisms and cells from populations thereof. U.S. Pat. No. 4,018,886 discloses small magnetic particles used to provide a large and widely distributed surface area for separating a select protein from a solution to enable detection thereof. The particles are coated with a protein that will interact specifically with the select protein.

U.S. Pat. No. 4,070,246 describes compositions comprising stable, water insoluble coatings on substrates to which biologically active proteins can be covalently coupled so that the resulting product has the biological properties of the protein and the mechanical properties of the substrate, for example, magnetic properties of a metal support.

A diagnostic method employing a mixture of normally separable protein-coated particles is discussed in U.S. Pat. No. 4,115,535. Microspheres of acrolein homopolymers and copolymer(s) with hydrophilic comonomers such as methacrylic acid and/or hyroxyethylmethacrylate are discussed in U.S. Pat. No. 4,413,070. U.S. Pat. No. 4,452,774 discloses magnetic iron-dextran microspheres which can be covalently bonded to antibodies, enzymes and other biological molecules and used to label and separate cells and other biological particles and molecules by means of a magnetic field. Coated magnetizable microparticles, reversible suspensions thereof, and processes relating thereto are disclosed in U.S. Pat. No. 4,454,234. A method of separating cationic from anionic beads in mixed resin beds employing a ferromagnetic material intricately incorporated with each of the ionic beads is described in U.S. Pat. No. 4,523,996. A magnetic separation method utilizing a colloid of magnetic particles is discussed in U.S. Pat. No. 4,526,681. U.K. Patent Application GB No. 2,152,664A discloses magnetic assay reagents.

An electron-dense antibody conjugate made by the covalent bonding of an iron-dextran particle to an antibody molecule is reported by Dutton, et al., Proc. Natl. Acad. Sci., 76, 3392–3396 (1979). Ithakissios, et al. describes the use of protein containing magnetic microparticles in radioassays in Clin. Chem., 23, 2072–2079 (1977). The separation of cells labeled with immunospecific iron dextran microspheres using high gradient magnetic chromatography is disclosed by Milday, et al., FEBS, 170, 232–238 (1984). In J. Immunol. Meth., 52, 353–367 (1982) Molday, et al. describe an immuno-specific ferromagnetic iron-dextran reagent for the labeling and magnetic separation of cells. An application of magnetic microspheres in labeling and separation of cells is also disclosed by Molday, et al. in Nature, 268, 437 (1977). A solid phase fluoroimmunoassay of human albumin and biological fluids is discussed by Margessi, et al., Clin. Chim. Acta., 89, 455–460 (1978). Nye, et al., Clin. Chim. Acta., 69, 387–396 (1976) disclose a solid phase magnetic particle radioimmunoassay. Magnetic fluids are described by Rosenweig, Scien. Amer., 252, 10,136–194 (1983). Magnetic protein A microspheres and their use in a method for cell separation are disclosed by Widder,et al., Clin. Immunol. and Immunopath., 14,395–400 (1979).

U.S. Pat. No. 5,279,936 is a method directed to the separation of a component of interest from other components of a mixture by causing the binding of the component of interest to magnetic particles. In the embodiment of the invention which is a method to separate cells from a mixture containing other components, the method comprises layering a first liquid medium containing cells and other components with a second medium which is of a different density than and/or different viscosity than the first liquid medium. The cells are bound to paramagnetic particles. The layered first liquid medium and the second liquid medium are subjected to a magnetic field gradient to cause the cell particles to migrate into the second medium. The purpose of isolating the cells in the second liquid medium is then, by a further embodiment, to separate the cells from the second liquid medium.

In the current invention, there is no need for a second liquid medium because the magnetic separation of HIV-1 infected cells is accomplished in the medium of phosphate buffered saline (PBS) diluted blood, by bringing the infected cells to a predetermined point in the reaction vessel. The only task required after separation is the illumination of the point of highest magnetic field concentration, to ascertain the presence or absence of high density specific fluorescence, which if present would indicate the presence of fluorescently tagged HIV-infected peripheral blood lymphocytes.

U.S. Pat. No. 4,935,147 is a method that specifically targets the application of magnetic separation in the assay of organic and inorganic biochemical analytes, particularly those analytes of interest in the analysis of body fluids. The method of this invention provides a way of separating non-magnetic particles from a medium by virtue of the chemically controlled non-specific reversible binding of such particles to magnetic particles. Because of the small size of the magnetic particles, it also provides for a very rapid binding of a substance to be separated. By then aggregating the particles there is provided a much more rapid and complete magnetic separation than has been achieved by previous methods.

In the current invention, this technique of magnetic separation does not apply because of the fact the antigen of interest is bound to cells, and therefore not in solution or in need of agglutination for separation. The current invention merely requires the adherence of the many magnetic particles to an infected cell surface to magnetically pull the entire cell of interest to a predetermined point in the reaction vessel for viewing.

OBJECTS AND ADVANTAGES

Accordingly, several objects and advantages of our invention are to provide a cost-effective, accurate means of early (within 4 days of exposure) HIV-1 infection detection in whole blood that was based on the ability to immunochemically/magnetically isolate and fluorescently label HIV-1 infected peripheral blood lymphocytes.

The advantages of the invention are:

1. Cell-bound antigen-based test closes the window period created by having to rely on the host immune system to produce antibodies against HIV-1 antigens to around 4 days.
2. Multi-purpose cartridge and fully automated incubator, magnetic separator and imaging system permit operation by non-medically trained personnel.
3. Appearance of cell-bound gp120 parallels appearance of viral genetic material, enabling invention to detect HIV presence in same time period as the current industry standard, the polymerase chain reaction (PCR) test at a small fraction of the cost.
4. Functional design of the multi-purpose cartridge permits a complete, self-contained, disposable unit that is much easier to handle than the PCR test for viral genetic material.
5. Entire test procedure requires minutes to turn around compared with weeks for PCR test.
6. Cost per test will be in tens of dollars rather than hundreds. Still further objects and advantages will become apparent from a consideration of the ensuing description and accompanying drawings.

REFERENCE NUMERALS

Figure 1:
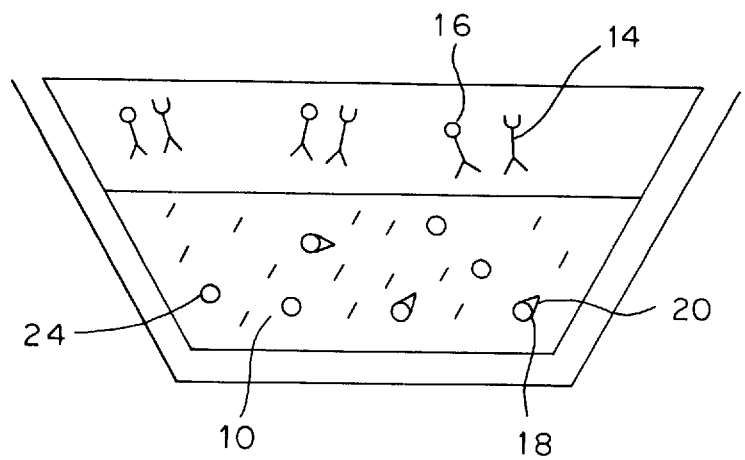
FIG. 1 shows reagents unmixed with whole blood.

10 Whole blood diluted in approximately 0.5 cc phosphate buffered saline (PBS)
14 Murine anti-gp120 monoclonal antibodies (mAbs) coupled to paramagnetic microspheres
16 Fluorescein conjugated anti-gp120 polyclonal antibodies (pAbs) IgG
HIV-infected peripheral blood lymphocytes
20 Exposed gp120 antigens
22 Antibodies non-competitively bound to the gp120 antigen on the HIV infected blood lymphocytes
24 Uninfected peripheral blood lymphocytes
26 Magnetic gradient
28 Focused light source.

PREFERRED EMBODIMENT—DESCRIPTION OF FIGS. 1 THROUGH 4

FIG. 1 shows the sample of several drops of whole blood diluted in approximately 0.5 cc PBS 10. To the diluted sample is added the Murine anti-gp120 monoclonal antibodies coupled to paramagnetic microspheres 14, and the Fluorescein conjugated anti-gp120 polyclonal antibodies IgG 16. In the sample of diluted whole blood are a small number of HIV-infected peripheral blood lymphocytes 18, bearing CD4, and also bearing numerous exposed gp120 antigens 20 (for simplicity, the Figures only display one gp120 antigen per peripheral blood lymphocyte).

Figure 2:
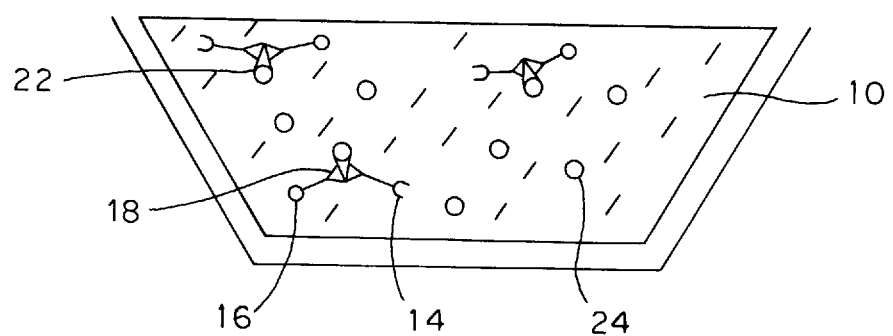
FIG. 2 shows reagents reacting with gp120 on surface of infected peripheral blood lymphocytes.

FIG. 2 shows the mixture of blood and antibodies after incubation for 5 minutes; both antibodies non-competitively bound to the gp120 antigen on the HIV infected blood lymphocytes 22. This renders each HIV infected peripheral blood lymphocyte 18 coated with both the Murine anti-gp120 monoclonal antibodies coupled to paramagnetic microspheres 14 and the Fluorescein conjugated anti-gp120 polyclonal antibodies IgG 16. The uninfected peripheral blood lymphocytes 24 remain uncoated by either of the antibodies.

Figure 3:
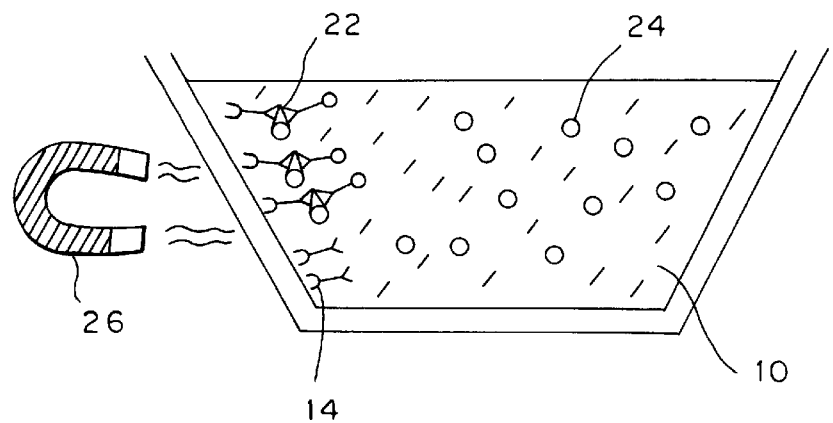
FIG. 3 shows magnetic field gradient separates tagged infected peripheral blood lymphocytes infected peripheral blood lymphocytes.

FIG. 3 shows the vessel containing the mixture of incubated whole blood diluted in approximately 0.5 cc phosphate buffered saline (PBS) 10 and reagents exposed to a strong magnetic gradient 26 at a predetermined point on the outer surface of the reaction vessel. The magnetic field causes the migration of antibodies non-competitively bound to the gp120 antigen on the HIV infected blood lymphocytes 22 to the inner surface of the reaction vessel at the maximum point of concentration of the magnetic gradient 26, thus separating the HIV-infected peripheral blood lymphocytes 18 from the uninfected peripheral blood lymphocytes 24 in the diluted whole blood sample. The magnetic separation takes approximately 20 seconds.

Figure 4:
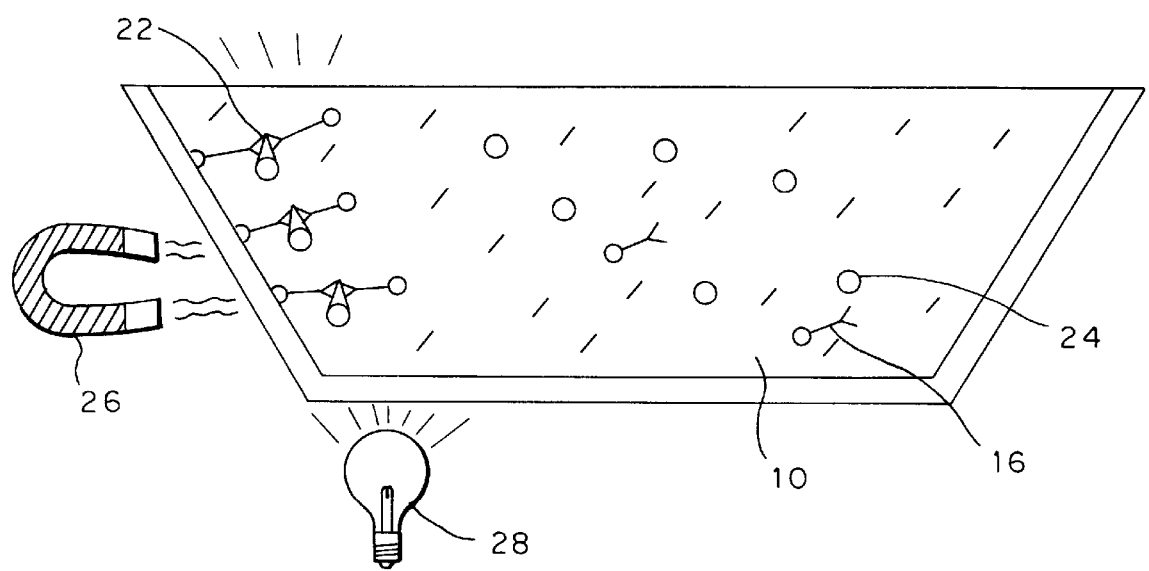
FIG. 4 shows separated infected fluorescent tagged peripheral blood lymphocytes illuminated and fluoresced by laser light.

FIG. 4 shows the vessel after the designated time for magnetic separation to occur. The predetermined point of maximum magnetic concentration at the gradient 26 is illuminated by a suitable focused light source 28 at 488 nm wavelength, causing all antibodies non-competitively bound to and to the gp120 antigen on the HIV infected blood lymphocytes 22 to glow and to separate from the uninfected peripheral blood lymphocytes 24 in the whole blood sample 10. Fluorescein conjugated anti-gp120 polyclonal antibodies IgG 16 provide a low intensity diffuse background fluorescence.

Reagents

1. Immunodiagnostics, Inc., Product #1121-M: Murine Anti-gp120 HIV-1 mAb Coupled to Paramagmetic Microspheres.

Previous Uses:
   a. B and T cell research
   b. Ultrastructural analysis
   c. B and T cell panning
   d. Immunoprecipitation These monoclonal antibodies of mouse origin are highly specific with high affinity to the gp120 HIV-1 glycoprotein. They are cross-reactive and cross-neutralizing antibodies, which are covalently bonded to paramagnetic microspheres. Their coupling ratio is approximately 2.5 micrograms of protein per milligram of magnetic microspheres. Specificity testing demonstrates that the Magnetic Murine anti-gp120 mAb binds recombinant gp120 (MN, IIIB) peroxidase conjugate as determined by ELISA. The biological activity is defined as the binding of these antibodies to CD-4 bearing, HIV-1 infected cells and HIV-1 infected human peripheral blood lymphocytes.

2. Immunodiagnostics, Inc. Product #1301-F: Fluorescein Rabbit Anti-gp120 HIV-1 IIIB pAb IgG.

Previous Uses:
   a. Dot Blot assays
   b. FACS
   c. Immunohistocytology
   d. Direct immunofluorescence assays These Fluorescein conjugated anti-gp120 (HIV-1 IIIB) pAb IgG were highly purified (95% pure) polyclonal IgG before use for FITC conjugation. The conjugate was then further purified by gel exclusion chromatography. The specificity of this fluorescein conjugated pAb IgG is defined by its binding to native and recombinant HIV-1 gp120 in Dot Blot assays and by its staining of cell surfaces in direct immunofluorescence assays. This reagent may be used for direct immunofluorescence assays. This reagent may be used for direct immuno-fluorescent staining of cells in the 1:50 dilution range, while Dot Blot assays with purified gp 120 may be performed at a minimum dilution of 1:100.

Both monoclonal and polyclonal antibodies bind to the V3 loop of the HIV-1 envelope glycoprotein gp120. The are not competitive, which means they attach to different regions of the V3 loop of gp120. This factor permits them to be used simultaneously for their specific and different purposes.

Preferred Embodiment—Operation

A sample of whole blood diluted in approximately 0.5 cc phosphate buffered saline 10 is combined with the reagents in a vessel. The first reagent consists of murine anti-gp120 monoclonal antibodies coupled to paragmagnetic microspheres 14. The second reagent consists of fluorescein conjugated anti-gp120 polyclonal antibodies IgG 16. The reagents are designed to bind themselves to HIV infected blood lymphocytes 18, bearing CD-4, which has numerous exposed gp120 antigens 20, which act as the connection points.

The mixture of blood and reagents is incubated at 37 degrees centigrade for approximately 5 minutes. After incubation the antibodies non-competitively bind to the gp120 antigen on the HIV infected blood lymphocytes 22. This renders each HIV infected peripheral blood lymphocyte 18 coated with both murine anti-gp120 monoclonal antibodies coupled to paramagnetic microspheres 14 and the fluorescein conjugated anti-gp120 polyclonal antibodies IgG 16. The uninfected peripheral blood lymphocytes 24 remain uncoated by either of the antibodies.

A strong magnetic gradient 26 is applied to a predetermined point on the outer surface of the vessel. The magnetic field causes migration of all antibodies non-competitively bound to the gp120 antigen on the HIV infected blood lymphocytes 22 to the inner surface of the vessel at the maximum point of concentration of the magnetic gradient 26, thus separating them from the uninfected peripheral blood lymphocytes 24 in the whole blood sample 10. The magnetic separation takes approximately 20 seconds.

After separation of antibodies non-competitively bound to the gp120 antigen on the HIV infected blood lymphocytes 22 from the uninfected peripheral blood lymphocytes 24, the predetermined point of maximum concentration of the magnetic gradient 26 is illuminated by a suitable focused light source 28 at 488 nm wavelength, causing all of the antibodies non-competitively bound to the gp120 antigen on the HIV infected blood lymphocytes 22 now aggregated at the predetermined point to glow at between 530–540 nm in fluorescent light.

Likewise, the excess of magnetic particles unbound immunologically to cell surfaces will travel at a much greater velocity to the inner surface of the vessel wall, assuring that before any cell coated with magnetic particles arrives at the vessel wall, there will have formed a dark coating of unbound Murine anti-gp120 monoclonal antibodies coupled to paramagnetic microspheres 14, against which the infected cells will adhere, also providing a nice contrast for the high density of glowing antibodies non-competitively bound to the gp120 antigen on the HIV infected blood lymphocytes 22. Polyclonal antibodies IgG 16 unbound to HIV infected peripheral blood lymphocytes 18 in the sample of diluted blood, are of a volume only sufficient to provide only a low intensity diffuse background fluorescence as compared to the high intensity of the antibodies non-competitively bound to the gp120 antigen on the HIV infected blood lymphocytes 22 visible by fluorescence microscopy on the infected cells adhering to the inner surface of the reaction vessel wall.

Conclusions, Ramifications, and Scope

Accordingly, it can be seen that we have developed a fluorometric immunological assay method for HIV-1 infection using two reagents: one coupled with paramagnetic microspheres and the other with an FITC to separate and identify the HIV-infected peripheral blood lymphocytes 18 in diluted whole blood 10 by separating the cells using a magnetic gradient 26 and causing them to fluoresce using a focused light source 28.

The advantages of the invention are:

a. Cell-bound antigen-based test closes the window period created by having to rely on the host immune system to produce antibodies against HIV-1 antigens to around 4 days.

b. Appearance of cell-bound gp120 parallels appearance of viral genetic material, enabling invention to detect HIV presence in same time period as the PCR test at a small fraction of the cost.

c. Entire test procedure requires minutes to turn around compared with weeks for PCR test.

d. Increased accuracy and low cost allow it to act as both screening and confirmatory test.

e. Can also be utilized in an automated format, utilizing a multi-purpose cartridge and fully automated incubator, magnetic separator and imaging system, permitting operation by non-medically trained personnel.

f. Test can be contained in a blood collection cartridge to permit complete, self-contained, disposable unit that is much easier to handle than the PCR test for viral genetic material.

Although the description above contains many specificities, these should not be construed as limiting the scope of the invention but as merely providing illustrations of some of the presently preferred embodiments of this invention. Various other embodiments and ramifications are possible within its scope. For example, the method can be used to test for other viral infections by varying the antibody combinations, or other fluorochromes could be utilized. The method can also be used test to for water contamination, or to separate and identify cancer cells.

Thus, the scope of the invention should be determined by the appended claims and their legal equivalents, rather than by the examples given.

We claim:

1. A method of detecting an HIV-infected cell in an aqueous sample comprising the steps of, a) combining a first anti-gp120 antibody attached to a magnetic particle; a second anti-gp120 antibody attached to a detectable label; and an aqueous sample containing HIV-infected peripheral blood lymphocytes displaying gp120 on the cell surface, to form a mixture;

b) incubating said mixture under conditions effective for binding of said antibodies to said gp120 to form a complex, said complex comprising said first and second antibody bound to a HIV-infected cell on said magnetic particle; and c) moving said magnetic particle to a predetermined point on a reaction vessel holding said mixture, wherein said moving is accomplished by a magnetic field acting on said magnetic particle;

d) detecting the label of said second antibody bound to gp120 on said HIV-infected cell, with the proviso that no step of washing of said mixture and no step of removing unbound first antibody and unbound second antibody from said mixture is performed in steps a), b), c), and d).

2. A method of claim 1, wherein said first and second antibody recognize different regions of gp120.

3. A method of claim 1, wherein said aqueous sample is whole blood.

4. A method of claim 1, wherein said predetermined point is illuminated with a light effective to detect said label.

5. A method of claim 1, wherein said detectable label is FITC.

6. A method of claim 1, wherein said first antibody is a monoclonal antibody.

7. A method of claim 1, wherein said second antibody is a polyclonal antibody.

8. A method of claim 1, where said first antibody is a monoclonal antibody and said second antibody is a polyclonal antibody coupled to a detectable label which is FITC.

9. A method of detecting an HIV-infected cell in an aqueous sample comprising the steps of, a) combining a first anti-gp120 antibody attached to a magnetic particle; a second anti-gp120 antibody attached to a detectable label; and an aqueous sample containing HIV-infected cells displaying gp120 on the cell surface, to form a mixture;

b) incubating said mixture under conditions effective for binding of said antibodies to said gp120 to form a complex, said complex comprising said first and second antibody bound to a HIV-infected cell on said magnetic particle; and c) moving said magnetic particle to a predetermined point on a reaction vessel holding said mixture, wherein said moving is accomplished by a magnetic field acting on said magnetic particle;

d) detecting the label of said second antibody bound to gp120 on said HIV-infected cell, with the proviso that no step of washing of said mixture and no step of removing unbound first antibody and second antibody from said mixture is performed in a), b), c), and d).

10. A method of claim 1, wherein said HIV-infected cell is a peripheral blood lymphocyte.

11. A method of claim 9, wherein said first and second antibody recognize different regions of gp120.

12. A method of claim 9, wherein said aqueous sample is whole blood.

13. A method of claim 9, wherein said predetermined point is illuminated with a light effective to detect said label.

14. A method of claim 9, wherein said detectable label is FITC.

15. A method of claim 9, wherein said first antibody is a monoclonal antibody.

16. A method of claim 9, wherein said second antibody is a polygonal antibody.

17. A method of claim 9, where said first antibody is a monoclonal antibody and said second antibody is a polyclonal antibody coupled to a detectable label which is FITC.

* * * * *